United States Patent [19]

Shimp

[11] Patent Number: 4,740,584
[45] Date of Patent: Apr. 26, 1988

[54] BLEND OF DICYANATE ESTERS OF DIHYDRIC PHENOLS

[75] Inventor: David Shimp, Prospect, Ky.

[73] Assignee: Interez, Inc., Jeffersontown, Ky.

[21] Appl. No.: 904,610

[22] Filed: Sep. 8, 1986

[51] Int. Cl.⁴ .................... C08G 73/06; C08G 83/00
[52] U.S. Cl. .............................. 528/422; 252/188.31; 528/210; 528/211; 528/373
[58] Field of Search ............... 528/422, 210, 211, 373; 252/188.31

[56] References Cited

U.S. PATENT DOCUMENTS 4,116,946  9/1978  Jakob et al. .......................... 528/422
4,528,366  7/1985  Woo et al. ........................... 528/422

Primary Examiner—Harold D. Anderson
Attorney, Agent, or Firm—Herbert P. Price

[57] ABSTRACT

Blends of ortho substituted dicyanate esters and unsubstituted dicyanate esters when partially reacted to form co-prepolymers are appreciably lower in viscosity at process temperatures than the homo-prepolymers of a particular dicyante. When cured, the blends exhibit excellent heat and moisture resistance properties. The cured compositions are useful in structural composites, filmed structural adhesives and printed wiring boards.

18 Claims, No Drawings

BLEND OF DICYANATE ESTERS OF DIHYDRIC PHENOLS

BACKGROUND OF INVENTION

The field of art to which this invention pertains is aryl cyanate esters, i.e., cyanic acid esters of polyhydric phenols.

Industry is constantly searching for lighter, stronger and more resistant materials to be used in place of the materials used today. For example, the aerospace industry is devoting considerable effort to utilizing structural composites in place of metals. Structural composites based on thermoplastic or thermoset resins and glass or carbon fibers have been and are being used successfully in many parts of military and commercial aircraft. Thermoset resins which are being used in such applications are epoxy resins, bismaleimide resins, and cyanate ester resins.

Cyanate ester resins, which are finding more and more uses, are based on the reaction products of polyhydric phenols and cyanogen halides. Such resins and their methods of preparation are described in U.S. Pat. Nos. 3,403,128 and 3,755,042. Additional patents which describe cyanate esters are U.S. Pat. Nos. 3,448,079, 3,987,230, 3,994,949, 4,022,755 and 4,330,658.

Such cyanate esters are generally crystalline in form but can be heated to form amorphous prepolymers which are partially trimerized resin intermediates. However, such homoprepolymers have a tendency to partially crystallize with time. Crystallized materials are difficult to handle in commercial operations and require extra heating to convert them to the amorphous form for ease of handling. Non-crystallizing homoprepolymers formed by increasing the degree of trimerization to 30 percent or greater have viscosities somewhat higher than prepreg manufacturers and fabricators of filament wound composites would like to use.

SUMMARY OF INVENTION

This invention relates to blends of cyanate esters. In one aspect this invention pertains to blends of (a) cyanate esters based on dihydric phenols which contain methyl substituents in the positions ortho to the phenolic hydroxyl groups and (b) cyanate esters based on dihydric phenols which contain no ortho substituents. In another aspect, this invention relates to prepolymers of the cyanate ester blends and to thermoset polymers obtained therefrom.

The ortho substituted cyanate esters used in this invention have the structural formula:

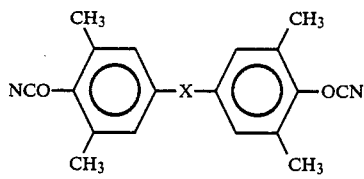

wherein X is methylene, isopropylidene, oxygen or divalent sulfur. These dicyanate esters are blended with dicyanate esters having the structural formula:

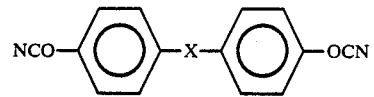

wherein X has the same definition as described hereinbefore. When heated at temperatures ranging from about 140° C. to about 240° C., the blended resins of this invention form non-crystallizing liquid and semisolid co-prepolymers which are appreciably lower in viscosity at process temperatures in the range of 20° C. to about 140° C. than are non-crystallizing homo-prepolymers.

When properly cured, the blended resins of this invention produce thermoset plastics which have superior hot-wet mechanical properties (heat deflection temperature, flexure strength and flexural modulus) and reduced moisture absorption as compared to one, and generally both, of the component dicyanate esters cured individually.

The compositions of this invention, particularly the co-prepolymers, find uses in the formulation of tacky/drapable prepregs for structural composite end use, tacky/compliant structural film adhesives, filament winding resins, pultrusion resins, high solids coatings and electrical insulating (impregnating) varnishes, die-attach adhesives and reaction injection molding compounds.

DETAILED DESCRIPTION OF INVENTION

The dicyanate esters useful in this invention are made by reacting a cyanogen halide with dihydric phenols in the presence of an acid acceptor, i.e., a base. This reaction is well known and is described in U.S. Pat. No. 3,755,402 which is hereby incorporated by reference. The cyanogen halides useful in this invention are cyanogen chloride and cyanogen bromide with cyanogen chloride being preferred.

The acid acceptors used to prepare dicyanate esters are inorganic or organic bases, such as sodium hydroxide, potassium hydroxide, sodium methylate, potassium methylate and various amines, preferably tertiary amines. Examples of useful amines are triethylamine, tripropylamine, diethylpropylamine, pyridine and the like. A preferred base is triethylamine.

The reaction is carried out in an organic solvent, such as ethylacetate, toluene, xylene, chlorinated hydrocarbons, acetone, diethylketone and the like. A preferred solvent is methylene chloride.

The reaction is conducted under low temperature conditions preferably between about −30° C. and 15° C.

The dicyanate esters useful in this invention are made by reacting dihydric phenols with cyanogen halide using the procedure described in U.S. Pat. No. 3,755,402 referred to hereinabove. Useful dihydric phenols for preparing the ortho substituted dicyanate esters are bis(4-hydroxy-3,5-dimethyl phenyl)methane, bis(4-hydroxy-3,5-dimethyl phenyl)-2,2-propane, bis(4-hydroxy-3,5-dimethylphenyl)ether and bis(4-hydroxy-3,5-dimethyl phenyl)sulfide. The preferred dihydric phenol is bis(4-hydroxy-3,5-dimethyl phenyl)methane.

The dicyanate esters which are blended with the dicyanate esters described above contain no ortho substituents adjacent to the phenolic hydroxy group. Such dicyanate esters are derived from dihydric phenols such as bis(4-hydroxyphenyl)methane, bis(4-hydroxyphenyl)-2,2-propane (Bisphenol A as it is commonly called), bis(4-hydroxyphenyl)ether and bis(4-hydroxyphenyl)sulfide.

The compositions of this invention are made by blending the dicyanate esters in the amounts of about 90 to about 10 parts by weight of ortho substituted dicyanate esters with about 10 to about 90 parts by weight of unsubstituted esters. Preferred blends comprise from about 30 to about 50 parts by weight of ortho substituted dicyanate ester with about 70 to about 50 parts by weight of unsubstituted dicyanate ester.

The blends of dicyanate esters can be used as is or can, preferably, be partially trimerized to form prepolymers. Prepolymers are amorphous in form and are somewhat easier to use in prepregging operations than the crystalline or semi-crystalline unpolymerized blends. Prepolymers are made by heating the blends with or without catalyst at a temperature of about 140° C. to about 240° C. for a time sufficient to cyclotrimerize from about 5 to about 50 percent of the cyanate functional groups and, preferably, about 15 to about 25 percent of the cyanate functional groups. Useful prepolymers possess melt viscosities ranging from about 1,000 cps. at 50° C. up to 60,000 cps. Catalysts which can be used in preparing the prepolymers are mineral or Lewis acids, bases such as alkali metal hydroxides, alkali metal alcoholates or tertiary amines, salts such as sodium carbonate or lithium chloride, or active hydrogen containing compounds, such as bisphenols and monophenols. It is preferred to conduct the prepolymerization reaction without a catalyst, utilizing only heat followed by thermal quenching, in the manner taught by British Pat. No. 1,305,762 which is hereby incorporated by reference.

Cyanate ester content can be determined quantitatively by infrared analysis or by "residual heat of reaction" using a differential scanning calorimeter. The percent trimerization is calculated by the formula $$\text{Percent Trimerization} = 100 \left[ \frac{\text{Wt}/OCN \text{ Monomer}}{\text{Wt}/OCN \text{ Prepolymer}} \times 100 \right]$$

wherein Wt/OCN is the equivalent weight per cyanate group.

Refractive index is directly related to the percent trimerization. A plot of refractive indices, taken at the same temperature, versus percent trimerization is linear. The slope of the plotted line will vary with the chemical composition of the particular cyanate ester or mixture being prepolymerized. By using these plots, the refractive index can be used to monitor the rate of reaction and the extent of the cyclotrimerization reaction.

The prepolymers of this invention are particularly useful in hot melt prepregging for aircraft structural composites. Hot melt prepregs are made by melting the prepolymer formulation and applying it as a film to release paper. Unidirectional carbon fibers are laid down on the hot sticky film and another release paper is placed on top of the film and fibers. The prepolymer and the fibers are then "worked" with pressure and motion to wet and coat the fibers with the prepolymer. The prepreg is then rolled up and is stored at 0° C. until needed for use. At 0° C., no reaction and no crystallization takes place. When needed, the prepreg is thawed to room temperature, is cut into various sizes and shapes and is laid-up on molds. For large structural composites, e.g., tail structure of aircraft, up to a week may be needed to complete the lay-up. If the prepregs crystallize during this time, they will become stiff and boardy and will be difficult to conform to the desired shape. At least one week of freedom from crystallization at room temperature to 120° F., the temperature range in which prepregs are usually applied to the mold, is desired by structural composite manufacturers.

The co-prepolymers of this invention are non-crystallizing liquids and semisolids which are appreciably lower in viscosity at process temperatures in the range of 20° C. to 140° C. than are the non-crystallizing homo-prepolymers.

The compositions of this invention in either unpolymerized or prepolymer form can be cured by heat alone but are preferably cured by the use of a catalyst plus heat. Such curing catalysts include those described above which are used in preparing prepolymers. Additional catalysts are those described in U.S. Pat. Nos. 3,962,184, 3,694,410 and 4,026,213 which are hereby incorporated by reference. Examples of such catalysts include zinc octoate, tin octoate, zinc stearate, tin stearate, copper acetylacetonate, phenol, catechol, triethylenediamine and chelates of iron, cobalt, zinc, copper, manganese and titanium with bidentate ligands such as catechol. Such catalysts are used in the amounts of about 0.001 to about 20 parts by weight per 100 parts by weight of the cyanate ester blend. A preferred catalyst system is that described in my copending patent application, Ser. No. 789,678, filed Oct. 21, 1985 now U.S. Pat. No. 4,604,452. Such catalysts are liquid solutions of a metal carboxylate and an alkylphenol, e.g., zinc napthenate and nonyl phenol. These catalyst are used in the amounts of about 0.001 to about 0.5 part by weight of metal and about 1 to about 20 parts by weight of alkylphenol per 100 parts by weight of cyanate ester blend.

The compositions of this invention are cured by heating at elevated temperatures for a time sufficient to obtain a complete cure, i.e., until at least about 80 percent of the cyanate functional groups are cyclotrimerized. The curing reaction can be conducted at one temperature or can be conducted by heating in steps. If conducted at one temperature, the temperature will vary from about 250° F. to about 450° F. When conducted by stepwise heating, the first step, or gelation step, is performed at a temperature of about 150° F. to about 350° F. The curing step is conducted at a temperature of about 300° F. to about 450° F., and the optional post-curing step is conducted at a temperature of about 400° F. to about 550° F. The overall curing reaction will take about 5 minutes to about 8 hours.

The dicyanate ester blends and coprepolymers of this invention have very good properties when cured. Surprisingly, it has been found that the cured blends have properties which exceed the properties of either of the esters when cured alone.

The dicyanate ester blends and coprepolymers of this invention can be blended with polyepoxide resins and can be cured to form useful thermoset compositions. Up to about 70 weight percent based on total blend weight can be polyepoxide resin. Such polyepoxide resins are the well-known glycidyl ethers of polyhydric phenols which are made by reacting an epihalohydrin, preferably epichlorohydrin, with a polyhydric phenol, preferably bisphenol A.

When formulating for particular end uses, additional components can be incorporated in the polycyanate composition. Such components include minor amounts of thermoplastic resin tougheners, reinforcing fibers, colloidal silica flow modifiers, mineral fillers and pigments.

The cured compositions of this invention can be used in vacuum bagged structural composites, transfer molded encapsulants, filmed structural adhesives, printed wiring boards and composites for aircraft primary structures.

The following examples will describe the invention in more detail. Parts and percentages unless otherwise indicated are parts and percentages by weight. BADCy referred to in the examples is bis(4-cyanatophenyl)-2,2-propane. METHYLCy is bis(4-cyanato-3,5-dimethylphenyl)methane.

EXAMPLE 1

BADCy and METHYLCy were heated to about 200° F. to about 250° F. to form blends. Catalyst solutions, blends of nonyl phenol and zinc napththenate, were then dissolved in the molten cyanate esters. After vacuum deairing, the catalyzed cyanate ester blends were poured into aluminum sheet molds preheated at 220° F. The molds were then heated to gel and cure the cyanate esters. The optically clear castings, ⅛ inch thick, were sawed and milled into test bars which were subjected to physical testing. The amounts of each of the components used to make the cured castings, the cure schedules and the results of the tests are listed in the following Table I.

TABLE I

| CURED-STATE PROPERTIES OF METHYLCy/BADCy BLENDS | | | | | | |
|---|---|---|---|---|---|---|
| Composition (Wt.) | 100/0 | 65/35 | 50/50 | 37/63 | 25/75 | 0/100 |
| METHYLCy (monomer) | 160 | 104 | 80 | 59.2 | 40 | — |
| BADCy (monomer) | — | 56 | 80 | 100.8 | 120 | 160 |
| Nonylphenol | 3.2 | 3.2 | 3.2 | 3.2 | 3.2 | 3.2 |
| Zinc Napthenate, 8% Zn | 0.30 | 0.23 | 0.20 | 0.20 | 0.20 | 0.20 |
| Minutes to Gel @ 250° F. | 25 | 15 | 20 | 15 | 15 | 15 |
| Cure Schedule | (1 hour @ 350° F. + 1 hour @ 420° F. + 2 hours @ 482° F.) | | | | | |
| Properties | | | | | | |
| HDT, °C. | | | | | | |
| Dry | 210 | >252 | >252 | 249 | >252 | 240 |
| Wet (1) | 204 | 237 | 236 | 218 | 211 | 200 |
| % H₂O Abs. (1) | 1.0 | 1.5 | 1.4 | 1.5 | 1.7 | 1.7 |
| Flexure Properties, Wet (2) Strength, KSI | | | | | | |
| at 77° F. | 16.7 | 14.5 | 19.0 | 19.2 | 15.5 | 20.0 |
| at 180° F. | 14.0 | 16.8 | 17.7 | 17.1 | 16.2 | 13.6 |
| at 270° F. | 12.2 | 13.8 | 13.8 | 12.7 | 12.3 | 11.6 |
| at 325° F. | 8.0 | 11.3 | 10.9 | 9.5 | 9.1 | 7.9 |
| Modulus, $10^6$ psi | | | | | | |
| at 77° F. | 0.42 | 0.41 | 0.41 | 0.44 | 0.45 | 0.47 |
| at 180° F. | 0.36 | 0.38 | 0.39 | 0.38 | 0.39 | 0.40 |
| at 270° F. | 0.33 | 0.31 | 0.30 | 0.29 | 0.30 | 0.33 |
| at 325° F. | 0.27 | 0.26 | 0.25 | 0.23 | 0.22 | 0.18 |
| Weight Loss (%) 120 hrs @ 400° F. | 0.14 | 0.32 | 0.37 | 0.40 | 0.48 | 0.61 |

(1) Moisture conditioned 64 hours at 200° F. + >95% RH.
(2) Moisture conditioned by boiling in water for 48 hours. Rapid (2-3 minute) heating of flexure bars prior to testing.

EXAMPLE 2

To a suitable reactor were added 390 parts of METHYLCy and 210 parts of BADCy. Heat, agitation and a nitrogen sparge were applied raising the temperature to 150° C. The rate of reaction and extent of reaction were determined by measuring the refractive index of the reactants at 110° C. The initial refractive index of the sample taken as soon as the 160° C. temperature was reached was 1.5276. Heating was continued at 160° C. for 2 hours and 40 minutes. The refractive index was 1.5286. Heating was then conducted for 40 minutes at 190° C. with the refractive index changing to 1.5295. The temperature was raised to 200° C. and was held at 200° C. for 20 minutes with the refractive index changing to 1.5307. The temperature was then raised to 210° C. and was held at 210° C. for 1 hour and 20 minutes. A sample of the reactants, Sample 1, had a refractive index of 1.5352. The percent trimerization was 11 percent. Samples were not taken until a drop of the prepolymer on a glass plate at room temperature did not crystallize in 20 minutes. Heating was continued at 210° C. for 1 hour and 10 minutes. The refractive index of Sample 2 was 1.5387. The percent trimerization was 16 percent. After an additional 50 minutes at 210° C., the refractive index of Sample 3 was 1.5418. The percent trimerization was 20.5 percent. The reactants were then cooled to room temperature. The final refractive index was 1.5425. The percent trimerization was 22 percent.

The viscosity of Sample 3 at 77° F. was 244,000 cps. The viscosity at 120° F. was 3,175 cps. At 150° F., it was 585 cps and at 180° F., it was 175 cps.

EXAMPLE 3

Using the same procedure described in Example 2, 300 parts of METHYLCy and 300 parts of BADCy were reacted. The refractive index of the initial blend again measured at 110° C. was 1.5295. After heating for 2 hours at 200° C., the refractive index was 1.5330. The temperature was increased to 210° C. and was held at this temperature for 1 hour and 40 minutes. The refractive index of Sample 1 taken at this time was 1.5364 The percent trimerization was 12 percent. Heating at approximately 210° C. was continued for 50 minutes. The refractive index of Sample 2 was 1.5397. The percent trimerization was 17 percent. After 1 hour additional heating at approximately 210° C., the refractive index of Sample 3 was 1.5427. The percent trimerization was 21 percent. The reactants were then cooled to room temperature. The final refractive index was 1.5456. The percent trimerization was 25 percent.

The viscosity of Sample 1 at 77° F. was 5,200 cps. The viscosity of Sample 2 at 77° F. was 8,900 cps. At 120° F., the viscosity was 559 cps. At 150° F., it was 161 cps and at 180° F., it was 60 cps. The viscosity of Sample 3 at 77° F. was 55,200 cps. At 120° F., the viscosity was 2,125 cps. At 150° F., it was 440 cps and at 180° F., it was 140 cps. The viscosity of the final product at 77° F. was 117,000 cps.

EXAMPLE 4

Using the same procedure described in Example 2, 222 parts of METHYLCy were reacted with 378 parts of BADCy. The initial refractive index measured at 110° C. was 1.5315. After heating for 40 minutes at 200° C., the refractive index was 1.5325. Heating was then continued at 210° C. for 1 hour and 40 minutes. The refractive index of Sample 1 taken at this time was 1.5410. The percent trimerization was 14 percent. After heating for an additional 55 minutes at 210° C., the refractive index of Sample 2 was 1.5444. The percent trimerization was 19 percent. Additional heating at 210° C. was continued for 40 minutes. The refractive index of Sample 3 was 1.5476. The percent trimerization was 22.5 percent. The reactants were then cooled. The final refractive index was 1.5500. The percent trimerization was 26 percent.

The viscosity of Sample 1 at 77° F. was 8,000 cps. The viscosity of Sample 2 at 77° F. was 48,800 cps. At 120° F., the viscosity was 1,550 cps. At 150° F., it was 350 cps and at 180° F., it was 120 cps. The viscosity of Sample 3 at 77° F. was 256,000 cps. At 120° F., the viscosity was 4,250. At 150° F., it was 900 cps and at 180° F. it was 235 cps.

EXAMPLE 5

Using the same procedure described in Example 2, the homoprepolymer was made with BADCy monomer. The initial refractive index of the BADCy monomer was 1.5333 measured at 110° C. After heating at 190° C. for 3 hours and 20 minutes, the refractive index of Sample 1 was 1.5559. The percent trimerization was 25 percent. After heating for 20 minutes at 180° C., the refractive index of Sample 2 was 1.5590. The percent trimerization was 28 percent. After additional heating for 40 minutes at 180° C., the refractive index of Sample 3 was 1.5622. The percent trimerization was 31.5 percent. The reactants were then cooled. The final refractive index was 1.5648 and the percent trimerization was 34 percent.

The viscosity of Sample 1 at 77° F. was 164,000 cps. The viscosity of Sample 2 at 77° F. was 352,000 cps. The viscosity of Sample 3 at 77° F. was 5,200,000 cps.

EXAMPLE 6

Using the same procedure described in Example 2 except without nitrogen sparging, METHYLCy monomer was homoprepolymerized. Nitrogen sparging was not used because pure METHYLCy prepolymerization with sparging requires a temperature well above 210° C. Without sparging, polymerization occurs at 180° C. to 210° C. The initial refractive index measured at 110° C. of the METHYLCy monomer was 1.5250. After heating for 4 hours and 15 minutes while raising the temperature slowly from 185° C. to 210° C., the refractive index of Sample 1 was 1.5382. The percent trimerization was 18 percent. After additional heating for 20 minutes at 205° C., the refractive index of Sample 2 was 1.5403. The percent trimerization was 21 percent. After additional heating for 30 minutes, the refractive index of Sample 3 was 1.5426. The percent trimerization was 25 percent. After additional heating for 20 minutes at 205° C., the reactants were cooled. The refractive index of the final material was 1.5461. The percent trimerization was 30 percent.

The viscosity of Sample 1 at 77° F. was 592,000 cps. The viscosity of Sample 2 at 77° F. was 2,040,000 cps. The viscosity of Sample 3 at 77° F. was 5,760,000 cps.

The properties, i.e., the percent trimerization, the viscosity and the tendency to crystallize at room temperature (R.T.) and at 120° F., of the prepolymers described in Examples 2-6 are listed in Table II.

TABLE II

| | Prepolymer Properties | | | |
|---|---|---|---|---|
| Sample | 1 | 2 | 3 | Final |
| Example 2 65 Wt Percent METHYLCy 35 Wt Percent BADCy | | | | |
| Percent Trimerization | 11 | 16 | 20.5 | 22 |
| Viscosity (cps) | | | | |
| at 77° F. | | | 244,000 | |
| at 120° F. | | 2,400 | 3,175 | 18,000 |
| at 150° F. | | | 585 | |
| at 180° F. | | | 175 | |
| Crystallization at R.T | | | | |
| 1 Day | 100% | Trace | None | None |
| 2 Days | | | | |
| 3 Days | | | | |
| 4 Days | | 100% | None | Trace |
| 5 Days | | | None | |
| 7 Days | | | None | 15% |
| 8 Days | | | 5% | 25% |
| 9 Days | | | | |
| 12 Days | | | 15% | 100% |
| 14 Days | | | 50% | |
| Crystallization at 120° F.* | | | | |
| 1 Day | 100% | None | None | None |
| 2 Days | | None | None | None |
| 5 Days | | 5% | None | None |
| 7 Days | | 10% | None | None |
| Example 3 50 Wt Percent METHYLCy 50 Wt Percent BADCy | | | | |
| Percent Trimerization | 12 | 17 | 21 | 25 |
| Viscosity (cps) | | | | |
| at 77° F. | 5,200 | 8,900 | 55,200 | 117,000 |
| at 120° F. | 875 | 559 | 2,125 | 19,750 |
| at 150° F. | | 161 | 440 | |
| at 180° F. | | 60 | 140 | |
| Crystallization at R.T. | | | | |
| 1 Day | None | None | None | None |
| 2 Days | | | | |
| 3 Days | None | None | None | None |
| 4 Days | Trace | Trace | Trace | Trace |
| 5 Days | 5% | Trace | Trace | Trace |
| 7 Days | 10% | 5% | Trace | Trace |
| 8 Days | | | | |
| 9 Days | | | | |
| 12 Days | 60% | 10% | 5% | 2% |
| 14 Days | 80% | 15% | 10% | 5% |
| Crystallization at 120° F.* | | | | |
| 1 Day | None | None | None | None |
| 2 Days | None | None | None | None |
| 5 Days | None | None | None | None |
| 7 Days | None | None | None | None |
| Example 4 37 Wt Percent METHYLCy | | | | |

TABLE II-continued

Prepolymer Properties

63 Wt Percent BADCy

| Percent Trimerization | 14 | 19 | 22.5 | 26 |
|---|---|---|---|---|
| Viscosity (cps) | | | | |
| at 77° F. | 8,000 | 48,800 | 256,000 | |
| at 120° F. | 1,200 | 1,550 | 4,250 | 46,000 |
| at 150° F. | | | 350 | 900 |
| at 180° F. | | | 120 | 235 |
| Crystallization at R.T. | | | | |
| 1 Day | None | None | None | None |
| 2 Days | None | None | None | None |
| 3 Days | None | None | None | None |
| 4 Days | None | None | None | None |
| 5 Days | | | | |
| 7 Days | None | Trace | None | None |
| 8 Days | | | | |
| 9 Days | None | Trace | None | None |
| 12 Days | | | | |
| 14 Days | None | Trace | None | None |
| Crystallization at 120° F.* | | | | |
| 1 Day | None | None | None | None |
| 2 Days | Trace | None | None | None |
| 5 Days | Trace | None | None | None |
| 7 Days | Trace | None | None | None |
| Sample | 1 | 2 | 3 | 4 |

Example 5
100 Wt. Percent BADCy

| Percent Trimerization | 25 | 28 | 31.5 | 34 |
|---|---|---|---|---|
| Viscosity (cps) | | | | |
| at 77° F. | 164,000 | 352,000 | 5,200,000 | — |
| at 120° F. | 5,700 | 14,750 | 67,000 | >100,000 |
| at 150° F. | | | | |
| at 180° F. | | | | |
| Crystallization at R.T. | | | | |
| 1 Day | None | None | None | None |
| 2 Days | Trace | Trace | None | None |
| 3 Days | 2% | 1% | None | None |
| 4 Days | 5% | 2% | None | Trace |
| 5 Days | | | | |
| 7 Days | | | | |
| 8 Days | | | | |
| 9 Days | 20% | 5% | Trace | Trace |
| 12 Days | | | | |
| 14 Days | | | | |
| Crystallization at 120° F.* | | | | |
| 1 Day | Trace | Trace | None | None |
| 2 Days | 1% | 1% | Trace | None |
| 5 Days | 1% | 1% | Trace | None |
| 7 Days | 2% | 1% | Trace | None |

Example 6
100 Wt Percent METHYLCy

| Percent Trimerization | 18 | 21 | 25 | 30 |
|---|---|---|---|---|
| Viscosity (cps) | | | | |
| at 77° F. | 592,000 | 2,040,000 | 5,760,000 | — |
| at 120° F. | 12,800 | 57,300 | >100,000 | >100,000 |
| at 150° F. | | | | |
| at 180° F. | | | | |
| Crystallization at R.T. | | | | |
| 1 Day | 100% | 10% | None | None |
| 2 Days | | 100% | Trace | None |
| 3 Days | | | 2% | None |
| 4 Days | | | | |
| 5 Days | | | | |
| 7 Days | | | | |
| 8 Days | | | 100% | 5% |
| 9 Days | | | | 100% |
| 12 Days | | | | |
| 14 Days | | | | |
| Crystallization at 120° F.* | | | | |
| 1 Day | 100% | 100% | 5% | Trace |
| 2 Days | | | 60% | 25% |
| 5 Days | | | 100% | 100% |
| 7 Days | | | | |

*Seeded with BADCy crystals.

The principles, preferred embodiments and modes of operation of the present invention have been described in the foregoing specification. The invention which is intended to be protected herein, however, is not to be construed as limited to the particular forms disclosed, since these are to be regarded as illustrating rather than restrictive. Variations and changes may be made by those skilled in the art without departing from the spirit of the invention.

What is claimed:

1. A curable composition consisting essentially of a blend of dicyanate esters in the amounts of about 90 to about 10 parts by weight of an ortho substituted dicyanate ester and about 10 to about 90 parts of an unsubstituted dicyanate ester, the total being 100 parts, wherein the ortho substituted dicyanate ester has the structural formula:

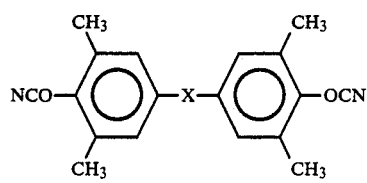

and the unsubstituted dicyanate ester has the structural formula:

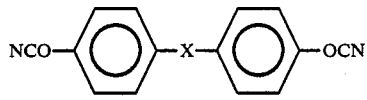

wherein X is methylene, isopropylidene, oxygen (—O—), or divalent sulfur (—S—).

2. The composition of claim 1 wherein the blend contains about 30 to about 50 parts by weight of ortho substituted dicyanate ester and about 70 to about 50 parts by weight of unsubstituted dicyanate ester.

3. The composition of claim 1 wherein the ortho substituted dicyanate ester is bis(4-cyanato-3,5-dimethylphenyl)methane.

4. The composition of claim 1 wherein the dicyanate ester is bis(4-cyanatophenyl)-2,2-propane.

5. A curable composition consisting essentially of a blend of dicyanate esters in the amounts of about 30 to about 50 parts by weight of bis(4-cyanato-3,5-dimethylphenyl)methane and about 70 to about 50 parts by weight of bis(4-cyanatophenyl)-2,2-propane, the total being 100 parts.

6. A prepolymer of the composition of claim 1 wherein about 5 percent to about 50 percent of the cyanate functional groups are cyclotrimerized.

7. A prepolymer of the composition of claim 1 wherein about 15 to about 25 percent of the cyanate functional groups are cyclotrimerized.

8. A prepolymer of the composition of claim 2 wherein about 5 percent to about 50 percent of the cyanate functional groups are cyclotrimerized.

9. A prepolymer of the composition of claim 2 wherein about 15 to about 25 percent of the cyanate functional groups are cyclotrimerized.

10. A prepolymer of the composition of claim 3 wherein about 5 percent to about 50 percent of the cyanate functional groups are cyclotrimerized.

11. A prepolymer of the composition of claim 3 wherein about 15 to about 25 percent of the cyanate functional groups are cyclotrimerized.

12. A prepolymer of the composition of claim 4 wherein about 5 percent to about 50 percent of the cyanate functional groups are cyclotrimerized.

13. A prepolymer of the composition of claim 4 wherein about 15 to about 25 percent of the cyanate functional groups are cyclotrimerized.

14. A prepolymer of the composition of claim 5 wherein about 15 to about 25 percent of the cyanate functional groups are cyclotrimerized and wherein said prepolymer has a viscosity of less than 60,000 cps at 50° C.

15. A cured composition obtained by heating the composition of claim 1 at a temperature of about 250° F. to about 550° F. until at least 80 percent of the cyanate functionality has been cyclotrimerized.

16. A cured composition obtained by heating the composition of claim 5 at a temperature of about 250° F. to about 550° F. until at least 80 percent of the cyanate functionality has cyclotrimerized.

17. A cured composition obtained by heating the prepolymer of claim 6 at a temperature of about 250° F. to about 550° F. until at least 80 percent of the cyanate functionality has been cyclotrimerized.

18. A cured composition obtained by heating the prepolymer of claim 14 at a temperature of about 250° F. to about 550° F. until at least 80 percent of the cyanate functionality has been cyclotrimerized.

* * * * *